United States Patent [19]

Inbar

[11] 4,001,591
[45] Jan. 4, 1977

[54] SCINTILLATION CAMERA AND HEAD THEREFOR HAVING MEANS FOR IMPROVING RESOLUTION OVER A LIMITED FIELD OF VIEW

[75] Inventor: Dan Inbar, Haifa, Israel
[73] Assignee: Elscint Ltd., Haifa, Israel
[22] Filed: July 11, 1975
[21] Appl. No.: 595,163
[52] U.S. Cl. .......................... 250/363 S; 250/366; 250/505
[51] Int. Cl.² ...................... G01T 1/20; G02B 5/00
[58] Field of Search ............... 250/363, 363 S, 366, 250/367, 361, 505, 515

[56] References Cited
UNITED STATES PATENTS 3,197,638   7/1965   Sinclair ............................ 250/274

Primary Examiner—Harold A. Dixon
Attorney, Agent, or Firm—Donald M. Sandler

[57] ABSTRACT

A head for a scintillation camera has a planar scintillating crystal that responds to radiation stimuli by producing light events whose spatial distribution corresponds to the spatial distribution of the radiation stimuli, and a plurality of photomultipliers each having a photocathode facing the crystal and producing an output signal when a light event occurs. The photomultipliers are organized into a first group arranged in a cluster centrally positioned relative to the crystal and having smaller photocathodes than those in the second group which is arranged in an annular array surrounding the first group. The head of the camera is connected to signal processing circuitry for computing each of two spatial coordinates of a light event by forming analytical functions of the output signals. Such circuitry has two selective modes of operation. In the first, each spatial coordinate of a light event is computed by forming an analytic function of the output signals from only those photomultipliers in the first group. In the second mode of operation, each spatial coordinate of the light event is computed using an analytical function of the sum of the output signals of the first group of photomultipliers and the output signals from the second group. For light events falling within a first portion of the crystal defined by the envelope of the projection on the crystal of the photocathodes of the first group of photomultipliers, when the signal processing circuitry is operating in its first mode, the resolution achieved will be much better than the resolution achieved when the signal processing circuitry is operating in its second mode.

17 Claims, 4 Drawing Figures

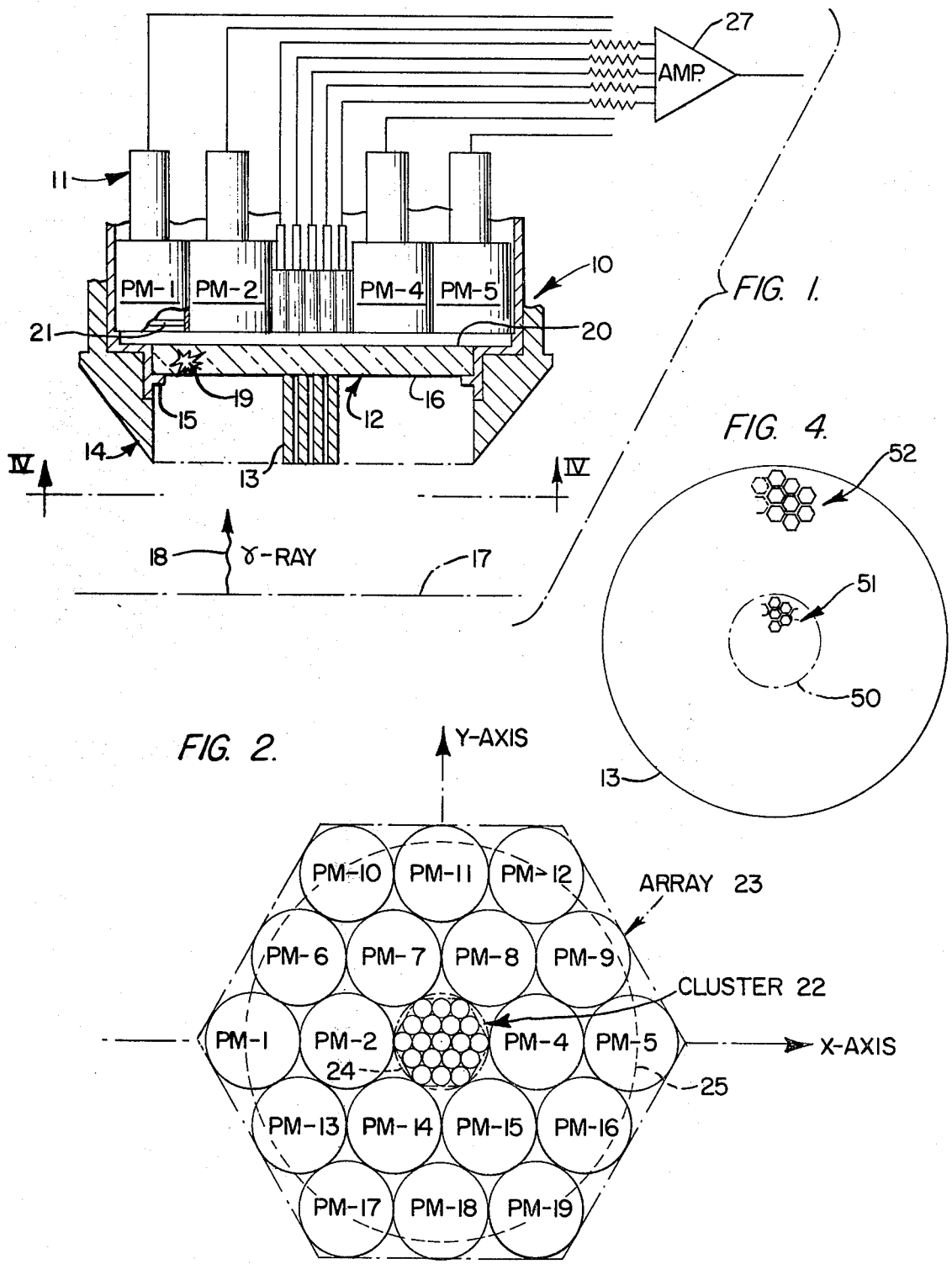

SCINTILLATION CAMERA AND HEAD THEREFOR HAVING MEANS FOR IMPROVING RESOLUTION OVER A LIMITED FIELD OF VIEW

This invention relates to scintillation cameras of the type disclosed in U.S. Pat. No. 3,011,056, issued to H. O. Anger, and U.S. Pat. No. 3,717,763 issued to Tanake et al, which patents are hereby incorporated by reference.

A scintillation camera of the type described in the Anger patent, hereinafter referred to as a scintillation camera of the type described, comprises a circular scintillating crystal, an array of photomultipliers positioned with their optical axis perpendicular to the plane of the crystal so that their photocathodes receive light from the crystal, and signal processing circuitry for operating on the output signals of the photomultipliers. When a radiation stimulus interacts with the lattice structure of the crystal, the resulting light event is seen by the photocathodes of the photomultipliers each of which produces an output signal related to the displacement of the light event from the photomultiplier. The signal processing circuitry is responsive to the output signals of the photomultipliers for computing the two spatial coordinates of the light event.

A conventional scintillation of the type described usually employs a 12-inch diameter crystal over which are positioned 19 3-inch diameter photomultipliers arranged in a 3-4-5-4-3 hexagonal pattern, or 37 two-inch diameter photomultipliers arranged in a 4-5-6-7-6-5-4 hexagonal pattern. While each pattern covers the entire crystal, the resolution available using the 37 photomultipliers is about 6mm. as compared with 7 or 8 mm. using the 19 photomultipliers.

Scintillation cameras of the type described are useful in nuclear medicine because they provide a tool for examining internal organs of the patient. To this end, a radioactive pharmaceutical with an affinity for the organ of interest is introduced into a patient's body causing a radiation field to be created within the organ. By positioning the crystal over the organ, and accumulating data from the camera over a predetermined period of time, the density distribution of the radiation field can be obtained in the form of a gray-scale or color-coded pattern of elemental areas covering the crystal Such a pattern contains significant medical information which can be interpreted by a trained observer in order to study, test and treat patients.

After a trained observer has had an opportunity to study the density distribution pattern of the radiation field, it is often discovered that limited portions thereof are more interesting from a medical point of view than others warranting a closer inspection. In order to evaluate such limited portions, their enlargement would be helpful. This can be achieved easily, for example, when the pattern is displayed on a television tube, but as the portion is enlarged, the resolution decreases thereby degrading the image and perhaps masking that which the observer wishes to study.

It is therefore an object of the present invention to provide a scintillation camera that achieves improved resolution over a limited region of interest thereby allowing enlargement of such region without loss of detail.

Briefly, the invention is based on the organization and size of the photomultipliers. Specifically, the photomultipliers are divided into two groups, the first group being arranged in a central cluster and having photocathodes smaller in size than those of the second group of photomultipliers, which are arranged in an annular array surrounding the cluster. The head of the camera is connected to signal processing circuitry for computing each of the two spatial coordinates of a light event. Such circuitry has two selective modes of operation. In the first, each spatial coordinate of a light event is computed by forming an analytical function of the output signals from only those photomultipliers in the first group. In the second mode of operation, each spatial coordinate of the light event is computed using an analytical function of the sum of the output signals of the first group of photomultipliers and the output signals from the second group. For light events falling within the first portion of the crystal defined by the envelope of the projections on the crystal of the photocathodes of the first group of photomultipliers when the signal processing circuitry is operating in its first mode, the resolution achieved will be much better than the resolution achieved when the signal processing circuitry is operating in its second mode. In this way, the resolution is improved over a field of view limited to said first portion of a crystal.

By arranging for the photomultipliers in each of the groups to be organized into similar patterns and locating the cluster in a position that would normally be occupied by a single photomultiplier in the array, it is possible to employ a single computer for computing the spatial coordinates of a light event regardless of the mode of operation. The two modes of operation of the signal processing circuit are achieved by means of a switching arrangement which applies, in the alternative, the outputs of the photomultipliers of the first group, or the outputs of the photomultipliers of the second group in combination with the sum of the outputs of the photomultipliers of the first group. Finally, the invention involves an improved collimator for use with the photomultipliers of the present invention.

An embodiment of the invention is illustrated by way of example in the accompanying drawings wherein:

FIG. 1 is a sectional view taken along the line I—I of FIG. 2 showing the head of a scintillation camera according to the present invention;

FIG. 2 is a plan view of the camera head according to the present invention utilizing the preferred type of photomultipliers;

FIG. 4 is a plan view of one form of collimator according to the present invention as seen from the line IV—IV in FIG. 1.

Figure 3:
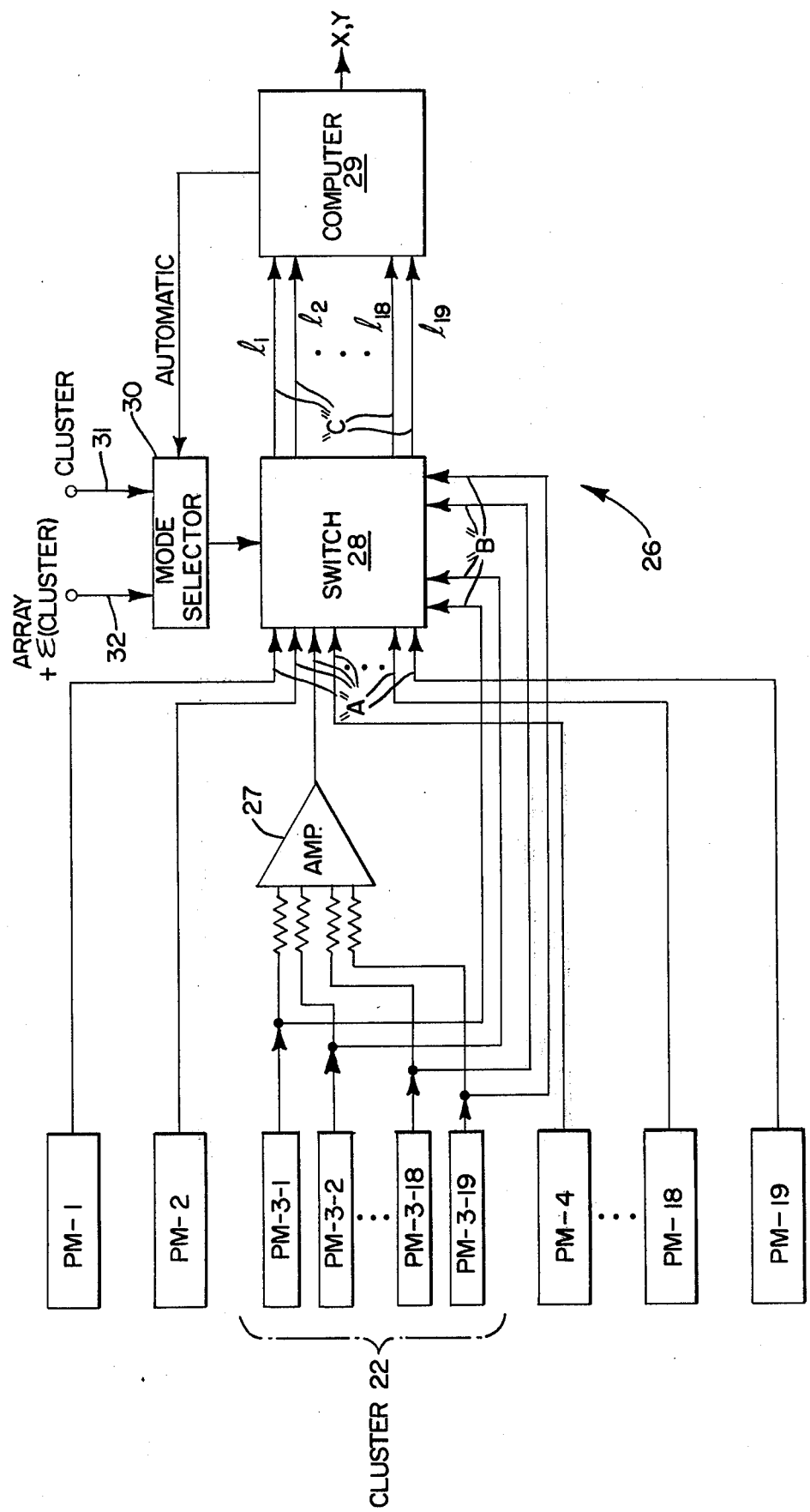
FIG. 3 is a block diagram of a complete scintillation camera according to the present invention.

Referring now to FIG. 1 of the drawings, reference numeral 10 designates a head for a scintillation camera according to the present invention comprising a plurality of photomultipliers, typically designated by reference numeral 11, scintillating crystal 12, collimator 13, and housing structure 14 by which the various components are held together in a unitary manner. Crystal 12 is a disc-shaped, planar, scintillating crystal, such as thallium-activated sodium-iodide, mounted in housing 14 by means of suitable shoulders 15. Such crystals are available in different sizes; and a convenient size in wide use at the present time for scintillation cameras of the type described is 12 to 16 inches in diameter.

Collimator 13, adjacent the input surface 16 of the crystal, is exposed to a radiation field 17, and has a plurality of holes, the axes of which are perpendicular to the plane of the crystal for limiting the field of view of the crystal. Details of the collimator are shown in FIG. 4. Only those gamma rays originating in the radiation field in a region directly beneath a hole and directed perpendicularly to the plane of the crystal pass through the hole and into the crystal. Gamma rays 18 emmanating from the radiation field 17 and passing through collimator 13 will enter the crystal 12 and interact with the lattice structure thereof at various depths thereby causing light events to occur at the sites of interaction. A typical light event is designated by reference numeral 19 in FIG. 1. By reason of the collimator, the spatial locations of light events in the crystal correspond to the spatial distribution of the radiation stimuli causing the events.

Light produced by a light event is radiated omnidirectionally from the interaction site in the crystal, and most of the light passes outwardly of the crystal through output surface 20 over which the photomultipliers 11 are positioned with their optical axis oriented in a direction perpendicular to the plane of the crystal. The photocathodes of the photomultipliers, typically illustrated by reference numeral 21, face the output surface 20, and are spaced therefrom to an extent that optimizes the geometrical sensitivity of the photomultipliers. A light event is thus seen by the photocathodes of each photomultiplier in both groups, the photomultiplier responding thereto by producing an output signal whose amplitude depends upon the displacement of the photomultiplier from the light event. As explained later, each spatial coordinate of a light event is computed from an analytical combination of the outputs of the photomultipliers.

Turning first to the organization and size of the photomultipliers, reference is made to FIG. 2 which shows how the photomultipliers are divided into two groups. The first group, designated generally by reference numeral 22, is arranged into a cluster disposed centrally over crystal 12 while the second group, designated generally by reference numeral 23, is arranged into an annular array surrounding the cluster. In the preferred embodiment of the invention, cluster 22 is composed of 19 photomultipliers that have one-half inch nominal diameter photocathodes, the photomultipliers being arranged in a 3-4-5-4-3 hexagonal pattern. These photomultipliers are designated PM-3-1 to PM-3-19 (see FIG. 3) for reference purposes. Array 23, on the other hand, is composed of 18 photomultipliers that have three-inch nominal diameter photocathodes arranged in a hexagonal pattern that is nominally a 3-4-5-4-3 pattern except that the central photomultiplier is missing defining or establishing a central opening in which cluster 22 is located. The photomultipliers of array 23 are designated PM-1, PM-2, and PM-4 to PM-19 as indicated in FIG. 3. Note the absence of a photomultiplier designated PM-3. Note also that cluster 22 occupies the same space as a photomultiplier with a 3-inch nominal diameter photocathode would occupy were the pattern of array 23 complete.

In the patterns of both the cluster 22 and the array 23, individual photomultipliers occupying the same relative location in each pattern bear the same index number. That is to say, the left-most photomultiplier lying along the X-axis in array 23 is designated PM-1 while the left most photomultiplier lying along the X-axis in array 22 is designated PM-3-1, etc.

Because of the different sizes of the photocathodes of the photomultipliers in cluster 22 and array 23, collimator 13 preferably is formed with two sets of holes, covering the cluster and array respectively. The inner set of holes 51 are contained within circle 50 congruent with circle 24 (FIG. 2), circle 50 being located in front of cluster 22. The cross-sectional area of the holes in circle 50 is much smaller than the cross-sectional area of the outer, annular set of holes 52 located in front of array 23.

The signal processing circuitry for computing the two coordinates of a light event in the crystal from the output signals of the various photomultipliers is designated generally by reference numeral 26 of FIG. 3 and comprises adder 27, switch 28 and computer 29. Switch 28 has two sets of 19 inputs termed the A and the B input terminals, and one set of nineteen outputs termed the C output terminals which are connected to nineteen inputs to computer 29 by the lines $l_1$ to $l_{19}$.

Switch 28 has two states as determined by mode selector 30 having manual inputs 31 and 32. When input 31 is actuated, the switch goes into its "high resolution" state wherein the respective C output terminals are connected to only the respective B input terminals, which are themselves directly connected to the respective outputs of the nineteen photomultipliers of cluster 22. That is to say, when the switch is in its high resolution state, photomultiplier PM-3-1 is connected to line $l_1$, etc. In such state, computer 29 is furnished with data from only the cluster 22.

Computer 29 may be of the type disclosed in FIG. 2 of the Anger patent or of the type disclosed in the Tanake et al patent referred to above. In the Anger patent, for example, computation of the displacement of a light event from each of the two orthogonal coordinate axis, designated the X-axis and Y-axis, is achieved by weighting the output signal obtained from each photomultiplier in accordance with its distance from the coordinate axis in question. The weighted sum of the photomultiplier output signals is used to calculate a coordinate of the light event (i.e., its displacement from a coordinate axis). Such weighted sum represents a fixes analytical function of the output signals. Mathematically, the coordinates $x$ and $y$ are:

$$x = f_x (b_1 s_1, \ldots, b_{19} s_{19});  \qquad (1)$$

and $$y = f_y (c_1 s_1, \ldots, c_{19} s_{19}) \qquad (2)$$

where the letters $b$ and $c$ represent the weights associated with the signals $s$ and each subscript represents the input line to the computer containing the signal in question.

By reason of the size of the photocathodes of the photomultipliers of cluster 22, a resolution of from 1 to 2 mm. can be achieved for events occuring within a field of view comprehended by the envelope of the projections of the photocathodes of the photomultipliers of cluster 22 on surface 20. Such envelope is suggested by the circular broken line 24 in FIG. 2, which is essentially congruent with circle 50, and constitutes what is termed hereinafter a "first portion of the output surface of the crystal."

When input 32 of mode selector switch 30 is actuated, the switch goes into its "normal" state wherein the respective C output terminals are connected to only the respective A input terminals to which are directly connected the respective outputs of the eighteen photomultipliers of array 23 and the output of adder 27. That is to say, photomultiplier PM-1 is connected to line $l_1$, etc. Line $l_3$ is not connected to a photomultiplier of array 23 since there is no photomultiplier PM-3. Instead line $l_3$ is connected to the output of adder 27 whose input comprises the outputs of the nineteen photomultipliers of cluster 22. Thus, the output of adder 27 (and hence the signal applied to line $l_3$) is the sum of the outputs of the photomultipliers of cluster 22. It appears to computer 29, when the switch is in its normal mode, that there are nineteen photomultipliers having relatively large, photocathodes of uniform area; size, and the mathmatical operations carried out by the computer, and expressed in equations (1) and (2) yield the coordinates $x$ and $y$ of a light event occurring anywhere within a field of view defined by the crystal as indicated by the circular broken line 25 in FIG. 2.

From the above description, it can be seen that the scintillation camera of the present invention will produce essentially a conventional display when the camera is operated in its normal mode. If an observer discovers a portion of the display that warrants further and closer inspection, a shift of the camera head can be made to locate the geometric center of the crystal directly above the centroid of the area of interest. In such position, the mode of operation can be changed to high resolution enabling the area of interest to be displayed using only the photomultipliers in cluster 22. As indicated previously, the resolution will be greater by reason of the density of photomultipliers within the area of circle 24 as compared to that in the annular area between circles 24 and 25. As a consequence, the image produced during the high resolution mode even when enlarged several times will have at least as good a resolution as the normal image obtained when the camera is operated in its normal mode.

Instead of computer 29 calculating each coordinate of a light event based on a fixed analytical function of signals appearing in lines $l_1$ to $l_{19}$ for each mode of switch 30, the analytical function can be made dependent on the spatial location of the light event in the crystal. Circuitry for the latter method of computation is disclosed in copending application Ser. No. 503,767 filed Sept. 6, 1974, in the names of J. Zioni et al, which application is hereby incorporated by reference. Furthermore, the circuitry shown in FIG. 3 can be modified so that the two modes of operation of switch 30 are combined into one. In such case, that portion of a radiation field seen by the portion of the crystal within the circle 24 (termed "first portion of the crystal") will be reproduced with a finer resolution dependent on the photomultipliers of cluster 22; while that portion of the field seen by the annular portion of the crystal between circles 24 and 25 (termed "second portion of the crystal") will be reproduced with the normal resolution available with the photomultiplier of array 23. Thus, the central portion of a display of the field will have a better resolution than the peripheral edges of the display. Finally, by utilizing the computing techniques in Zioni et al application Ser. No. 503,767, each spatial coordinate of a light event is computed by forming different functions of the output signals of the photomultipliers depending upon whether the light event occurs in the first or second portions of the crystal.

Patterns other than hexagonal can be used; and indeed the patterns need not be the same for each group of photomultipliers. If the patterns are not similar, separate computing circuits will be required.

Finally, in its broadest aspect, the present invention requires that the density of photomultipliers over one portion of the crystal be different from the density over a second portion. Mathematically, the density is expressed as the ratio $n:A$ where $n$ represents the number of photomultipliers in a portion and A represents the total area of their photocathodes. In the present case, it is necessary for $n_1/A_1$ to exceed $n_2/A_2$ where $n_1$ and $n_2$ are the respective numbers of photomultipliers in the first and second portions (i.e., within circle 24 on the one hand and within circles 24 and 25 on the other) of the crystal $A_1$ and $A_2$ are the respective total areas of the two areas of the two sets of photomultipliers. If $n_2/A_2$ exceeds $n_1/A_1$, the annular region of the crystal will have a greater resolution than the central region.

While it facilitates design of the signal processing circuitry when the photocathode area of each photomultiplier of a set is uniform, uniformity is not necessary. Where uniformity is present, then the number of photomultipliers in one set must exceed the number of photomultipliers in the other set. In each case, if the area of each photocathode in the group having a total area $A_1$ is $a_1$, and $a_2$ is the area of each photocathode in the group having a total area $A_2$, then it follows that $a_2$ must be greater than $a_1$ if $n_1/A_1$ is to exceed $n_2/A_2$.

What is claimed is:

1. A head for a scintillation camera comprising:
  a. a scintillating crystal having an input surface exposed to radiation stimuli for producing light events at spatial locations corresponding to spatial locations of the interactions of the stimuli with the crystal, and an output surface opposite the input surface;
  b. a plurality of photomultipliers each having a photocathode facing the output surface of the crystal and producing an output signal when a light event occurs; and
  c. means mounting the photomultipliers in two different groups, a first group forming a cluster of $n_1$ photomultipliers whose photocathodes have a total area of $A_1$, and a second group forming an array of $n_2$ photomultipliers whose photocathodes have a total area $A_2$ wherein $n_1/A_1$ is greater than $n_2/A_2$.

2. A head for a scintillation camera according to claim 1 including a collimator positioned between the crystal and the source of radiation stimuli, said collimator having two sets of holes of different sizes, the set having the smaller size holes overlying the $n_1$ photomultipliers in the first group and the set having the larger size holes overlies the $n_2$ photomultipliers in the second group.

3. A head for a scintillation camera according to claim 1 wherein each photocathode of the photomultipliers in the first group has area $a_1$, and each photocathode of the photomultipliers in the second group has area $a_2$ where $a_2$ is greater than $a_1$.

4. A head for a scintillation camera according to claim 3 wherein the area of the envelope of the projections on said output surface of the photocathodes of the first group encompasses a first portion of said output surface, the area of said first portion being approximately equal to $a_2$.

5. A scintillation camera including the head of claim 4 in combination with signal processing circuitry for computing each spatial coordinate of a light event by forming different functions of the output signals of the photomultipliers depending upon whether the light event occurs in the first or second portions.

6. A head for the scintillation camera according to claim 4 wherein the envelope of the projections on said output surface of the photocathodes of the second group encompasses a second portion of said output surface which is separate from the first portion, the second portion being annular with a circular opening of the same size as the first portion which is located in such opening.

7. A head for a scintillation camera according to claim 4 wherein the photomultipliers in each group are arranged in the same pattern, the pattern of the second group having a vacancy within which the first group fits.

8. A head for a scintillation camera according to claim 7 wherein the first group of photomultipliers is located at the geometric center of the second group of photomultipliers.

9. A head for a scintillation camera according to claim 8 wherein $n_1 = n_2 + 1$.

10. A scintillation camera including the head of claim 9 in combination with signal processing circuitry having computing means with $n_1$ input lines by which input signals are applied to said computing means which is responsive thereto for forming at least one analytical combination of said input signals for each spatial coordinate, adder means to combine the output signals $n_1$ photomultipliers of the first group for forming a sum signal, and means for selectively applying to the $n_1$ input lines either the output signals of the $n_1$ photomultipliers of the first group, or the output signals of the $n_2$ photomultipliers of the second group as well as the sum signal.

11. A scintillation camera including the head of claim 4 in combination with signal processing circuitry responsive to the output signal of the photomultiplier for computing the two spatial coordinates of the light event in the crystal using analytical functions of said signals.

12. A scintillation camera according to claim 11 wherein the signal processing circuitry has a first mode of operation in which output signals from only those photomultipliers in the first group are used for computing each spatial coordinate of a light event.

13. A scintillation camera according to claim 12 wherein the said signal processing circuitry has a second mode of operation in which output signals from both groups of photomultipliers are used for computing each spatial coordinate of a light event.

14. A scintillation camera according to claim 13 including means for selecting a mode of operation of said signal processing circuitry.

15. A scintillation camera according to claim 14 wherein the signal processing circuitry includes adder means to combine the output signals of the first group of photomultipliers for forming a sum signal, and means for computing each spatial coordinate of a light event by forming an analytical function of the sum signal and the output signals of the second group of photomultipliers.

16. A head for scintillation camera comprising:
a. a scintillating crystal having an input surface exposed to radiation stimuli and an output surface;
b. a plurality of photomultipliers each having a photocathode facing the output surface of the crystal; and
c. means mounting the photomultipliers in two groups, each of the photocathodes of the photomultipliers in one group having the same area, each of the photocathodes of the photomultipliers in the other group having the same area, the area of each photocathode of the one group being smaller than the area of each photocathode of the other group.

17. A collimator for use with a scintillation camera head comprising a structure having a first set of uniform holes, and a second set of uniform holes, the holes of the second set being larger than and arranged annularly around the holes of the first set which are arranged in a central cluster.

* * * * *